United States Patent
Tzeng et al.

(10) Patent No.: US 7,763,633 B2
(45) Date of Patent: Jul. 27, 2010

(54) INDOLO[3,2-C]QUINOLINE COMPOUNDS

(75) Inventors: Cherng-Chyi Tzeng, Kaohsiung (TW); Yeh-Long Chen, Kaohsiung (TW); Jing-Jer Lin, Taipei (TW); Chih-Ming Lu, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 12/421,193

(22) Filed: Apr. 9, 2009

(65) Prior Publication Data

US 2009/0298846 A1 Dec. 3, 2009

Related U.S. Application Data

(60) Provisional application No. 61/043,907, filed on Apr. 10, 2008.

(51) Int. Cl.
*A61K 31/4745* (2006.01)
*C07D 471/06* (2006.01)

(52) U.S. Cl. .................. 514/285; 546/70; 546/62; 544/361; 514/253

(58) Field of Classification Search .............. 514/285, 514/232.8, 253; 546/70, 62; 544/125, 361
See application file for complete search history.

(56) References Cited

FOREIGN PATENT DOCUMENTS

EP   0 226 508 A1 * 6/1987

OTHER PUBLICATIONS

Molina, P. et al.: New methodology for the preparation of pyrrole and indole derivatives via iminophosphoranes: synthesis of pyrroloquinoxalines, indoloquinolines and indoloquinazolines. Tetrahedron, vol. 46, pp. 1063-1078, 1990.*

Chen, et al., "*Synthesis and Cytotoxic Activity Evaluation of Indolo-, Pyrrolo-, and Benzofuro-Quinolin-2(IH)-Ones and 6-Anilinoindoloquinoline Derivatives*", Bioorganic & Medicinal Chemistry 10 (2002) 2705-2712.

Hu, et al., "*A Novel Indoloquinoline Derivative, IQDMA, Induces S-Phase Arrest and Apoptosis in Promyelocytic Leukemia HL-60 Cells*", Cell Biol Toxicol 2006; 22:417-427.

Lin, et al., "*Induction of G2/M Phase Arrest and Apoptosis by a Novel Indoloquinoline Derivative, IQDMA, INK562 Cells*", Drug Development Research 67:743-751 (2006).

* cited by examiner

*Primary Examiner*—Charanjit S Aulakh
(74) *Attorney, Agent, or Firm*—Occhiuti Rohlicek & Tsao LLP

(57) ABSTRACT

Indolo[3,2-c]quinoline compounds of formula (I) shown below. Each variable in this formula is defined herein. These compounds can be used to inhibit both growth of cancer cells and activity of telomerase.

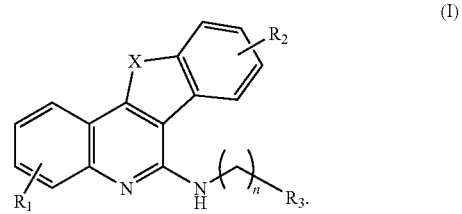

(I)

15 Claims, No Drawings

INDOLO[3,2-C]QUINOLINE COMPOUNDS

CROSS-REFERENCE TO RELATED APPLICATION PARAGRAPH

This application claims the benefit of U.S. Provisional Application No. 61/043,907 filed on Apr. 10, 2008, the content of which is hereby incorporated by reference in its entirety.

BACKGROUND

Ever since isocryptolepine, one of the indolo[3,2-c]quinoline-type alkaloids, was isolated from *Cryptoleptis sanguinolenta* (a plant used in traditional medicine against malaria), several indolo[3,2-c]quinoline compounds have been synthesized and extensively studied as potential antiplasmodial agents. See, e.g., Timari, G. et al., *Synlett.* 1997, 1067; Devaraj, R. et al., *Bioorg. Med. Chem. Lett.* 1997, 7, 369; Xiao, Z. et al., *Bioorg. Med. Chem.* 2001, 11, 2875-2878; Kumar, R. N. et al., *Tetrahedron Lett.* 2002, 43, 3327; Mulwad, V. V. et al., *Indian J. Chem. Section B*, 2003, 42B, 1937; and Miert, S. V. et al., *J. Nat. Prod.* 2005, 68, 674-677. Some indolo[3,2-c]quinoline compounds were prepared and evaluated for anticancer effects. See, e.g., Chen, Y. L. et al., *Bioorg. Med. Chem.* 2002, 10, 2705; Lin, Y. H. et al., *Drug Dev. Res.* 2006, 67, 743; and Hu, X. W. et al., *Cell Biol. Toxicol.* 2006, 22, 417. Indolo[3,2-c]quinoline compounds have a tetracyclic heterocycle that can intercalate into the double helix of DNA to block DNA replication or transcription, resulting in inhibition of tumor cell growth. See, e.g., Molina, A, et al., *J. Org. Chem.* 1996, 61, 5587.

SUMMARY

This invention relates to certain indolo[3,2-c]quinoline compounds that can be used to inhibit both growth of cancer cells and activity of telomerase, a common target for treating cancer.

In one aspect, this invention features indolo[3,2-c]quinoline compounds of formula (I):

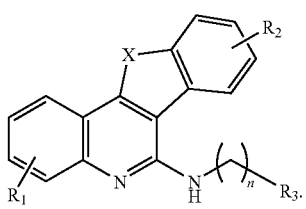

(I)

In this formula, X is O, S, NH, hydroxyimino, or alkoxyimino; $R_1$ is H, halo, alkyl, OH, alkoxyl, nitro, amino, alkylamino, or dialkylamino; $R_2$ is H, halo, alkyl, nitro, amino, alkylamino, or dialkylamino; $R_3$ is H, alkyl, aryl, heteroaryl, cycloalkyl, heterocycloalkyl, amino, or —N(A)-B; in which A is H, alkyl, aryl, heteroaryl, cycloalkyl, or heterocycloalkyl; and B is alkyl optionally containing 1-6 N atoms, aryl, heteroaryl, cycloalkyl, or heterocycloalkyl; or A, B, and the N atom to which they are attached together are heterocycloalkyl or heteroaryl; and n is 1, 2, 3, or 4.

Referring to formula (I), a subset of the indolo[3,2-c]quinoline compounds described above are those in which $R_3$ is aryl, heteroaryl, cycloalkyl, heterocycloalkyl, amino, or —N(A)-B. In these compounds, X can be NH, hydroxyimino, or alkoxyimino; $R_3$ can be aryl or —N(A)-B in which A, B, and the N atom to which they are attached together are heterocycloalkyl or heteroaryl; more specifically, $R_3$ can be phenyl, piperazinyl, or morpholinyl; or $R_3$ can be amino or —N(A)-B in which A is H, alkyl, aryl, heteroaryl, cycloalkyl, or heterocycloalkyl and B is alkyl containing 1-6 N atoms, aryl, heteroaryl, cycloalkyl, or heterocycloalkyl; B can be alkyl containing 1-6 N atoms; more specifically, B can be of formula (II):

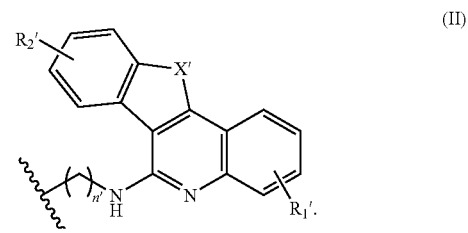

(II)

In formula (II), X' is O, S, NH, hydroxyimino, or alkoxyimino; each of $R_1'$ and $R_2'$, independently, is H, halo, alkyl, OH, alkoxyl, nitro, amino, alkylamino, or dialkylamino; and n' is 1, 2, 3, or 4.

In another aspect, this invention features indolo[3,2-c]quinoline compounds of formula (I) shown above, except that each of $R_1$ and $R_2$, independently, is H, halo, alkyl, OH, alkoxyl, nitro, amino, alkylamino, or dialkylamino; and $R_3$ is H, alkyl, aryl, heteroaryl, cycloalkyl, heterocycloalkyl substituted with alkyl, or —N(A)-B; in which A is H, alkyl, aryl, heteroaryl, cycloalkyl, or heterocycloalkyl; and B is alkyl containing 1-6 N atoms, aryl, heteroaryl, cycloalkyl, or heterocycloalkyl; or A, B, and the N atom to which they are attached together are heterocycloalkyl substituted with alkyl or heteroaryl.

Referring to formula (I), a subset of the indolo[3,2-c]quinoline compounds described immediately above are those in which $R_3$ is aryl, heteroaryl, heterocycloalkyl substituted with alkyl, or —N(A)-B in which A, B, and the N atom to which they are attached together are heterocycloalkyl or heteroaryl. Another subset of the indolo[3,2-c]quinoline compounds described above are those in which $R_3$ is amino or —N(A)-B in which A is H, alkyl, aryl, heteroaryl, cycloalkyl, or heterocycloalkyl and B is alkyl containing 1-6 N atoms, aryl, heteroaryl, cycloalkyl, or heterocycloalkyl.

The term "compound" used herein refers to both compounds and ions. For example, when —NH— on the quinoline side chain is replaced by —$NH_2^+$—, the compound of formula (I) is a cation. The term "alkyl" refers to a saturated, linear or branched hydrocarbon moiety containing 1-20 carbon atoms (e.g., $C_1$-$C_{10}$), such as —$CH_3$ or —$CH(CH_3)_2$. The term "alkoxyl" refers to an —O-alkyl. The term "alkoxyimino" refers to an —N(O-alkyl)-. The term "cycloalkyl" refers to a saturated, cyclic hydrocarbon moiety having 3 to 30 carbon atoms (e.g., $C_3$-$C_{12}$), such as cyclohexyl. The term "heterocycloalkyl" refers to a saturated cyclic moiety, such as a 5-8 membered monocyclic, 8-12 membered bicyclic, or 11-14 membered tricyclic ring system that has at least one ring heteroatom (e.g., N, O, or S), e.g., 4-tetrahydropyranyl. The term "aryl" refers to a hydrocarbon moiety having one or more aromatic rings, such as a 6-carbon monocyclic, 10-carbon bicyclic, or 14-carbon tricyclic aromatic ring system. Examples of aryl moieties include phenyl (Ph), phenylene, naphthyl, naphthylene, pyrenyl, anthryl, and phenanthryl. The term "heteroaryl" refers to a moiety having one or more aromatic rings, such as a aromatic 5-8 membered monocyclic, 8-12 membered bicyclic, or 11-14 membered tricyclic ring system that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "alkenyl" refers to a linear or branched hydrocarbon moiety containing 2-20 carbon atoms (e.g., $C_2$-$C_{10}$) and at least one double bond, such as —CH=CH—CH$_3$. The term "alkynyl" refers to a linear or branched hydrocarbon moiety containing 2-20 carbon atoms (e.g., $C_2$-$C_{10}$) and at least one triple bond, such as —C≡C—CH$_3$. The term "cycloalkenyl" refers to a non-aromatic, cyclic hydrocarbon moiety having 3 to 30 carbon atoms (e.g., $C_3$-$C_{12}$) and at least one double bond, such as cyclohexenyl. The term "heterocycloalkenyl" refers to a non-aromatic, cyclic moiety such as a non-aromatic 5-8 membered monocyclic, 8-12 membered bicyclic, or 11-14 membered tricyclic ring system having at least one ring heteroatom (e.g., N, O, or S) and at least one ring double bond, e.g., pyranyl.

Alkyl, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl include all of the above-recited substituents except $C_1$-$C_{10}$ alkyl. Cycloalkyl, heterocycloalkyl, aryl, and heteroaryl can also be fused with each other.

In still another aspect, this invention features a synthetic processes for preparing an indolo[3,2-c]quinoline compound of formula (I). The process includes reacting a 5,11-dihydroindolo[3,2-c]quinolin-6-one with POCl$_3$ to form a 6-chloro-11H-indolo[3,2-c]quinoline; and reacting the 6-chloro-11H-indolo[3,2-c]quinoline with a substituted amine to form an indolo[3,2-c]quinoline compound of formula (I).

In yet another aspect, this invention features a method of inhibiting DNA replication or transcription in a tumor cell. The method includes contacting the tumor cell with an effective amount of one or more indolo[3,2-c]quinoline compounds of formula (I) shown above.

Also within the scope of this invention is a method for treating cancer. The method includes administering to a subject in need thereof an effective amount of one or more indolo[3,2-c]quinoline compounds of formula (I) shown above. Examples of cancer that can be treated by the indolo[3,2-c]quinoline compounds of this invention include but are not limited to leukemia, colon cancer, lung cancer, melanoma, and breast cancer. The term "treating" or "treatment" refers to administering one or more indolo[3,2-c]quinoline compounds to a subject, who has one of the above-described diseases, a symptom of or a predisposition toward such a disease, with the purpose to confer a therapeutic effect, e.g., to cure, relieve, alter, affect, or ameliorate the disease.

In addition, this invention features a pharmaceutical composition that contains at least one of the above-mentioned indolo[3,2-c]quinoline compounds for use in treating cancer, as well as this therapeutic use and use of the compounds for the manufacture of a medicament for the just-mentioned treatment.

The indolo[3,2-c]quinoline compounds described above include the compounds themselves, as well as their salts, prodrugs, and solvates, if applicable. A salt, for example, can be formed between an anion and a positively charged group (e.g., amino) on an indolo[3,2-c]quinoline compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a indolo[3,2-c]quinoline compound. Suitable cations include sodium ion, potassium ion, magnesium ion, calcium ion, and an ammonium cation such as tetramethylammonium ion. The indolo[3,2-c]quinoline compounds also include those salts containing quaternary nitrogen atoms. Examples of prodrugs include esters and other pharmaceutically acceptable compounds, which, upon administration to a subject, are capable of providing active indolo[3,2-c]quinoline compounds. A solvate refers to a complex formed between an active indolo[3,2-c]quinoline compound and a pharmaceutically acceptable solvent. Examples of pharmaceutically acceptable solvents include water, ethanol, isopropanol, ethyl acetate, acetic acid, and ethanolamine.

The details of one or more embodiments of the invention are set forth in the description below. Other features, objects, and advantages of the invention will be apparent from the description and from the claims.

DETAILED DESCRIPTION

The indolo[3,2-c]quinoline compounds described above can be prepared by methods well known in the art. Scheme 1 shown below illustrates a typical synthetic route for synthesizing certain exemplary indolo[3,2-c]quinoline compounds. $R_1$ and $R_2$ in this scheme can be those described in the Summary section above.

Scheme 1

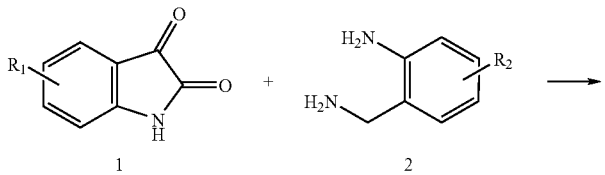

-continued
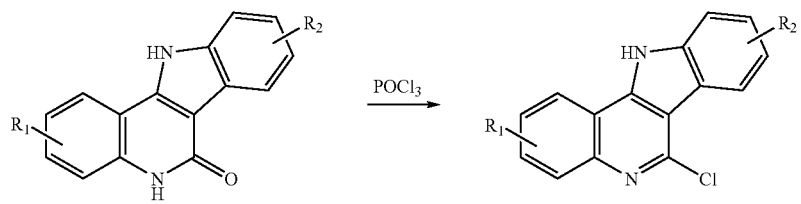
3a R₁ = R₂ = H
3b R₁ = F, R₂ = H
3c R₁ = Cl, R₂ = H
3d R₁ = OCH₃, R₂ = H
3e R₁ = NO₂, R₂ = H
4a R₁ = R₂ = H
4b R₁ = F, R₂ = H
4c R₁ = Cl, R₂ = H
4d R₁ = OCH₃, R₂ = H
4e R₁ = NO₂, R₂ = H
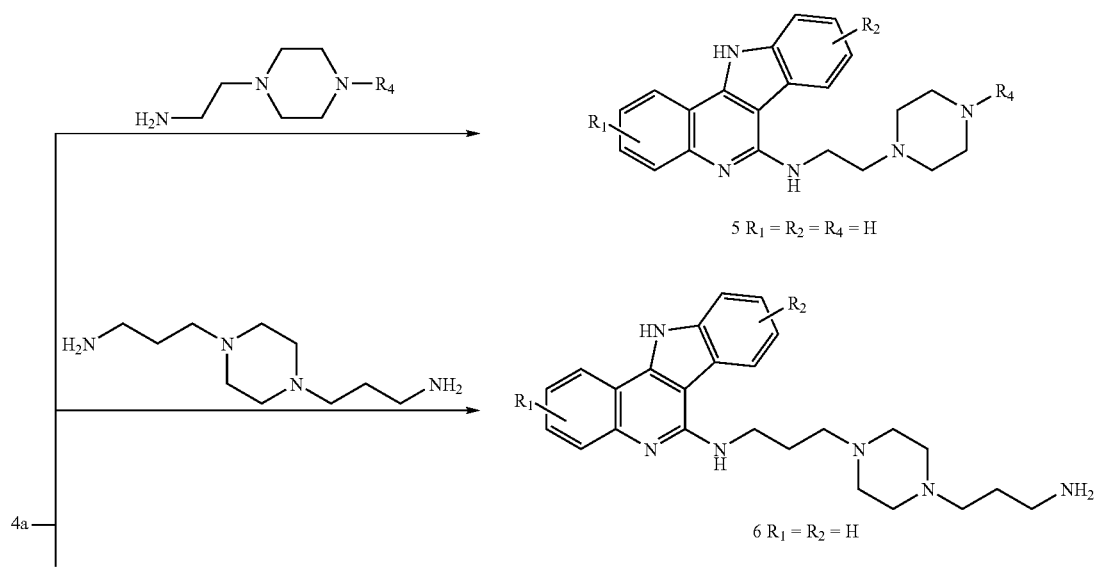
5 R₁ = R₂ = R₄ = H
6 R₁ = R₂ = H
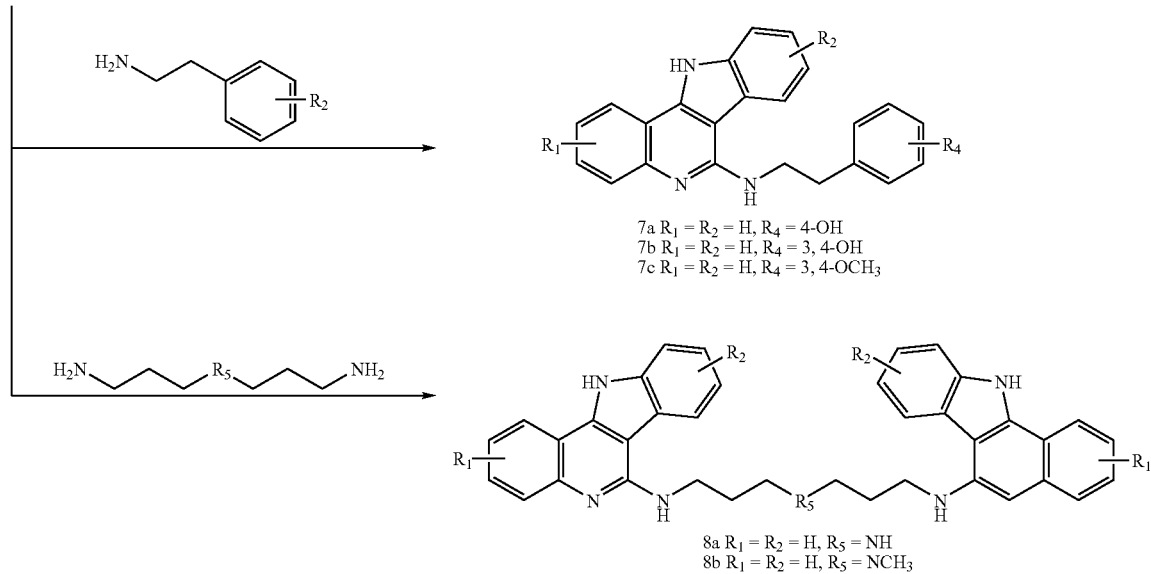
7a R₁ = R₂ = H, R₄ = 4-OH
7b R₁ = R₂ = H, R₄ = 3, 4-OH
7c R₁ = R₂ = H, R₄ = 3, 4-OCH₃
8a R₁ = R₂ = H, R₅ = NH
8b R₁ = R₂ = H, R₅ = NCH₃

Specifically, as shown in Scheme 1 above, reaction of substituted isatin 1 and 2-aminobenzylamine 2 can produce 5,11-dihydroindolo[3,2-c]quinolin-6-ones 3, which can be treated with POCl₃ to afford the corresponding 6-chloro-11H-indolo[3,2-c]quinolines 4. Treatment of compound 4 with substituted amines can lead to the formation of an indolo[3,2-c]quinoline compound of this invention.

Shown below are 7 exemplary compounds of this invention:

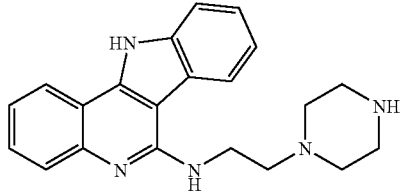
5

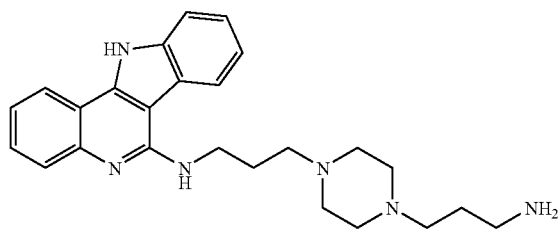
6

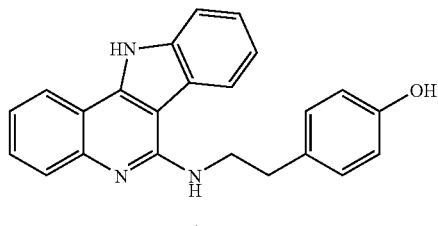
7a

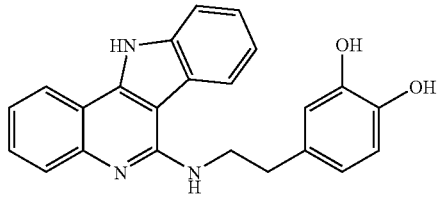
7b

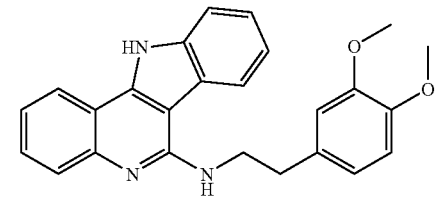
7c

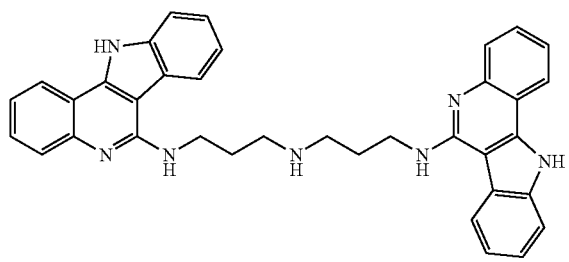
8a

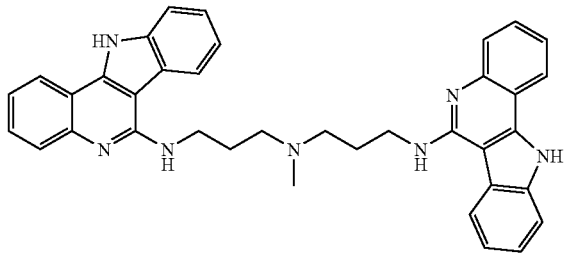
8b

The indolo[3,2-c]quinoline compounds described above can be prepared by methods well known in the art. Examples 1-9 below provide detailed descriptions of how these compounds were actually prepared.

An indolo[3,2-c]quinoline compound synthesized above can be purified by a suitable method such as column chromatography, high-pressure liquid chromatography, or recrystallization.

Other indolo[3,2-c]quinoline compounds can be prepared using other suitable starting materials through the above synthetic routes and others known in the art. The methods described above may also additionally include steps, either before or after the steps described specifically herein, to add or remove suitable protecting groups in order to ultimately allow synthesis of the indolo[3,2-c]quinoline compounds. In addition, various synthetic steps may be performed in an alternate sequence or order to give the desired compounds. Synthetic chemistry transformations and protecting group methodologies (protection and deprotection) useful in synthesizing applicable indolo[3,2-c]quinoline compounds are known in the art and include, for example, those described in R. Larock, *Comprehensive Organic Transformations*, VCH Publishers (1989); T. W. Greene and P. G. M. Wuts, *Protective Groups in Organic Synthesis*, 2nd Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The indolo[3,2-c]quinoline compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition containing at least one indolo[3,2-c]quinoline compound described above and a pharmaceutical acceptable carrier. Further, this invention covers a method of administering an effective amount of one or more of the indolo[3,2-c]quinoline compounds to a patient having cancer. "An effective amount" refers to the amount of an active indolo[3,2-c]quinoline compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of the present invention, a composition having one or more indolo[3,2-c]quinoline compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active indolo[3,2-c] quinoline compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active indolo[3,2-c]quinoline compound. Examples of other carriers include colloidal silicon oxide, magnesium stearate, cellulose, sodium lauryl sulfate, and D&C Yellow # 10.

The indolo[3,2-c]quinoline compounds described above can be preliminarily screened for their efficacy in treating above-described diseases by in vitro assays (see Examples 10 and 11 below) and then confirmed by clinic trials. Other methods will also be apparent to those of ordinary skill in the art.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Preparation of Compound 3b:
2-Fluoro-5,1,1-dihydro-indolo[3,2-c]quinolin-6-one

A mixture of 5-fluoroisatin (1, $R_1$=F, 1.65 g, 10 mmol) and 2-aminobenzylamine (2, 2.44 g, 20 mmol) was refluxed in acetic acid (50 mL) for 4 h. The reaction mixture was poured into water and the solid formed was collected by filtration. The crude product was heated in ethanol and filtered to give 3b. Yield: 1.45 g (57%); Mp: >350° C.

$IR_{\nu max}$ (cm$^{-1}$): 1622, 3240 in KBr.
$^1$H NMR (DMSO-d$_6$) δ: 7.30 (m, 1H), 7.39-7.45 (m, 2H), 7.51 (dd, 1H, J=4.8, 8.8 Hz), 7.66 (d, 1H, J=8.4 Hz), 8.02 (dd, 1H, J=2.8, 9.6 Hz), 8.23 (d, 1H, J=7.6 Hz), 11.54 (br s, 1H), 12.60 (br s, 1H).
$^{13}$C NMR (DMSO-d$_6$) δ: 107.08, 107.45 (J=24.2 Hz), 111.84, 112.60 (J=9.1 Hz), 117.04 (J=24.3 Hz), 117.94 (J=8.4 Hz), 120.97, 121.27, 124.22, 124.44, 134.64, 137.75, 139.95 (J=3.1 Hz), 156.98 (J=235.7 Hz), 159.65.

Elemental weight percentage calculated for $C_{15}H_9FN_2O$: C, 71.42; H, 3.60; N, 11.11. Found: C, 71.11; H, 3.80; N, 10.92.

Example 2

Preparation of Compound 4b:
6-Chloro-2-fluoro-11H-indolo[3,2-c]quinoline

A mixture of 3b (1.51 g, 6.0 mmol) and POCl$_3$ (30 mL) was refluxed for 8 h. After cooling, the mixture was poured into ice-water (150 mL) and an aqueous solution of concentrated NaOH was added until pH 10 was reached. The resulting precipitate was collected by filtration, washed with H$_2$O, and then recrystallized from MeOH/DMF to give 4b (1.48 g, 91%); Mp: 250-251° C.;

$UV_{\lambda max}$ nm (log ε): 233 (4.31), 267 (4.45), 290 (4.05), 340 (3.50) in MeOH; $IR_{\nu max}$ (cm$^{-1}$): 1357, 1512 in KBr.
$^1$H NMR (DMSO-d$_6$) δ: 7.44 (m, 1H, Ar—H), 7.61 (m, 1H, Ar—H), 7.68 (ddd, 1H, J=3.2, 8.8, 9.2 Hz, C (3)-H), 7.79 (m, 1H, Ar—H), 8.11 (dd, 1H, J=5.6, 8.8 Hz, C (4)-3H), 8.30 (dd, 1H, J=2.4, 9.2 Hz, C (1)-H), 8.43 (m, 1H, Ar—H).
$^{13}$C NMR (DMSO-d$_6$) δ: 106.46 (J=24.2 Hz), 111.59, 112.30, 117.30 (J=10.6 Hz), 118.50 (J=25.3 Hz), 120.58, 121.42 (J=2.3 Hz), 126.43, 131.18 (J=10.1 Hz), 138.80, 141.31, 141.45, 141.50, 143.92, 159.53 (J=243.3 Hz).

Elemental weight percentage calculated for $C_{15}H_8ClN_2 \cdot 0.3H_2O$: C, 65.23; H, 3.14; N, 10.14. Found: C, 65.21; H, 3.52; N, 10.20.

Example 3

Preparation of Compound 5: N-(11H-Indolo[3,2-c]quinolin-6-yl)-2-(piperazin-1-yl)ethanamine A mixture of 4a (1.26 g, 5 mmol) and 1-(2-aminoethyl) piperazine (1.94 g, 15 mmol) in 2-ethoxyethanol (50 mL) was heated at 140-150° C. for 48 h (by TLC monitoring). The mixture was then cooled and evaporated in vacuo to give a residue which was dissolved in EA (50 mL). The EA layer was washed with H$_2$O, brine, dried (MgSO$_4$), and concentrated. The residue was dissolved in MeOH (10 mL) and a solution of 6N HCl was added at 0° C. The reaction mixture was then stirred at room temperature for 8 h. The resulting precipitate was collected by filtration, washed with MeOH, and dried at 90° C. under reduced pressure for 24 h to produce the hydrochloride of compound 5, which was further purified by FC (MeOH/CH$_2$Cl$_2$=1/10 to 1/3) to afford 5 (0.51 g, 29%) as an orange color powder. Mp: 210-211° C.

UV$_{\lambda max}$ nm (log ε): 256 (4.61), 296 (4.10), 336 (3.86), 347 (3.85) in MeOH; IR$_{\mu max}$ (cm$^{-1}$): 3402 in KBr.

$^1$H NMR (DMSO-d$_6$) δ: 2.47 (m, 4H, piperazinyl-H), 2.68 (t, 2H, J=6.4 Hz, NHCH$_2$CH$_2$N), 2.77 (m, 4H, piperazinyl-H), 3.77 (m, 2H, NHCH$_2$CH$_2$N), 6.56 (t, 1H, J=4.8 Hz, NH), 7.30 (m, 2H, Ar—H), 7.43 (m, 1H, Ar—H), 7.50 (m, 1H, Ar—H), 7.67 (m, 2H, Ar—H), 8.25 (m, 2H, Ar—H), 12.50 (br s, 1H, NH).

$^{13}$C NMR (200 MHz, DMSO-d$_6$) δ: 37.37, 45.85 (2C), 54.01 (2C), 57.27, 102.70, 111.68, 114.17, 120.02, 120.26, 120.88, 121.38, 121.58, 123.98, 126.28, 128.08, 138.19, 140.69, 146.14, 152.91.

Elemental weight percentage calculated for C$_{21}$H$_{23}$N$_5$.1.0H$_2$O: C, 69.40; H, 6.93; N, 19.27. Found: C, 69.68; H, 6.92; N, 19.00.

Example 4

Preparation of Compound 6: {3-[4-(3-Aminopropyl) piperazin-1-yl]propyl} (11H-indolo[3,2-c]quinolin-6-yl)amine and its hydrochloride Compound 6 and its hydrochloride were obtained from 4a and 1,4-bis(3-aminopropyl)piperazine in a manner similar to that described in Example 3. The hydrochloride was purified by FC (MeOH/CH$_2$Cl$_2$=1/10 to 1/3) to produce 6 as an orange color powder. Yield: 32%; Mp: 87-88° C.

UV$_{\lambda max}$ nm (log ε): 260 (4.65), 337 (3.84) in MeOH; IR$_{vmax}$ (cm$^{-1}$): 1621, 1645, 3389 in KBr.

$^1$H NMR (DMSO-d$_6$) δ: 1.63 (quin., 2H, J=6.8 Hz), 1.92 (quin., 2H, J=6.8 Hz), 2.27-2.48 (m, 12H), 2.72 (t, 2H, J=7.2 Hz), 3.40 (br s, 2H, NH$_2$), 3.73 (m, 2H), 6.66 (br s, 1H, NH), 7.29 (m, 2H), 7.42 (m, 1H), 7.49 (m, 1H), 7.65 (m, 2H), 8.27 (dd, 1H, J=1.2, 8.0 Hz), 8.37 (d, 1H, J=8.0 Hz), 12.58 (br s, 1H, NH), 14.05 (br s, 1H, HCl).

$^{13}$C NMR (200 MHz, DMSO-d$_6$) δ: 25.92, 26.03, 38.39, 38.61, 52.51 (2C), 52.93 (2C), 55.06, 56.46, 102.59, 111.33, 114.01, 119.91, 120.59, 120.81, 121.28, 121.51, 123.75, 126.06, 127.88, 137.98, 140.61, 145.98, 152.83.

Elemental weight percentage calculated for C$_{25}$H$_{32}$N$_6$.1.6HCl.1.4H$_2$O: C, 60.04; H, 7.34; N, 16.80. Found: C, 59.82; H, 7.42; N, 16.79.

Example 5

Preparation of Compound 7a: 6-[2-(4-Hydroxyphenyl)ethylamino]-11H-indolo[3,2-c]quinoline and its hydrochloride Compound 7a and its hydrochloride were obtained from 4a and 4-(2-aminoethyl)phenol in a manner similar to that described in Example 3. The hydrochloride was purified by recrystallization with MeOH to produce 7a as a white powder. Yield: 40%; Mp: 320-321° C.

UV$_{\lambda max}$ nm (log ε): 227 (4.50), 256 (4.62), 323 (4.01), 338 (4.12) in MeOH; IR$_{vmax}$ (cm$^{-1}$): 1610, 1645, 3415 in KBr.

$^1$H NMR (DMSO-d$_6$) δ: 3.03 (t, 2H, J=7.4 Hz), 4.13 (m, 2H), 6.69 (m, 2H), 7.19 (m, 2H), 7.45 (m, 1H), 7.58 (m, 2H), 7.78 (m, 2H), 8.32 (d, 1H, J=8.4 Hz), 8.38 (br s, 1H, NH), 8.52 (m, 2H), 9.29 (br s, 1H, OH), 12.47 (br s, 1H, NH), 13.80 (br s, 1H, HCl).

$^{13}$C NMR (200 MHz, DMSO-d$_6$) δ: 33.69, 43.96, 100.16, 112.74, 113.08, 115.14 (2C), 118.74, 120.73, 121.20, 122.04, 122.79, 124.94, 125.74, 128.39, 129.96 (2C), 130.72, 135.21, 138.56, 141.42, 149.16, 155.93.

Elemental weight percentage calculated for C$_{23}$H$_{19}$N$_3$O.1.0HCl.1.2H$_2$O: C, 67.14; H, 5.49; N, 10.21. Found: C, 67.14; H, 5.47; N, 10.20.

Example 6

Preparation of Compound 7b: 6-[2-(3,4-Dihydroxyphenyl)ethylamino]-11H-indolo[3,2-c]quinoline and its hydrochloride Compound 7b and its hydrochloride were obtained from 4a and 2-(3,4-dihydroxyphenyl)ethylamine in a manner similar to that described in Example 3. The hydrochloride was purified by FC (MeOH/CH$_2$Cl$_2$=1/10) and recrystallization with MeOH to produce 7b as a white powder. Yield: 15%; Mp: 202-203° C.

UV$_{\lambda max}$ nm (log ε) 241 (4.52), 271 (4.67), 337 (3.99), 350 (4.08) in MeOH; IR$_{vmax}$ (cm$^{-1}$): 1613, 1647, 3417 in KBr.

$^1$H NMR (DMSO-d$_6$) δ: 2.96 (t, 2H, J=7.4 Hz), 4.08 (m, 2H), 6.66 (m, 2H), 6.80 (d, 1H, J=1.6 Hz), 7.44 (m, 1H), 7.58 (m, 2H), 7.78 (m, 2H), 8.32 (d, 1H, J=7.6 Hz), 8.35 (br s, 1H, NH), 8.50 (d, 1H, J=8.0 Hz), 8.54 (d, 1H, J=8.0 Hz), 8.80 (br s, 1H, OH), 8.84 (br s, 1H, OH), 12.44 (br s, 1H, NH), 13.80 (br s, 1H, HCl).

$^{13}$C NMR (200 MHz, DMSO-d$_6$) δ: 33.88, 43.93, 100.22, 112.66, 112.80, 115.51, 116.45, 118.86, 119.62, 120.74, 121.19, 121.95, 122.78, 124.81, 125.64, 129.14, 130.64, 138.53, 141.37, 143.81, 145.18, 149.24, 155.96.

Elemental weight percentage calculated for C$_{23}$H$_{19}$N$_3$O$_2$.1.0HCl.2.0H$_2$O: C, 62.52; H, 5.47; N, 9.51. Found: C, 62.58; H, 5.45; N, 9.63.

Example 7

Preparation of Compound 7c: 6-[2-(3,4-Dimethoxyphenyl)ethylamino]-11H-indolo[3,2-c]quinoline and its hydrochloride Compound 7c and its hydrochloride were obtained from 4a and 2-(3,4-dimethoxyphenyl)ethylamine in a manner similar to that described in Example 3. The hydrochloride was purified recrystallization with MeOH to produce 7c as a white powder. Yield: 66%; Mp: 231-232° C.

UV$_{\lambda max}$ nm (log ε): 229 (4.40), 258 (4.69), 323 (3.96), 338 (4.08) in MeOH; IR$_{vmax}$ (cm$^{-1}$): 1645, 1612, 3411 in KBr.

$^1$H NMR (DMSO-d$_6$) δ: 3.07 (t, 2H, J=7.4 Hz), 3.01 (s, 3H), 3.65 (s, 3H), 4.23 (m, 2H), 6.78 (d, 1H, J=8.0 Hz), 6.86 (dd, 1H, J=1.6, 8.0 Hz), 7.05 (d, 1H, J=1.6 Hz), 7.44 (m, 1H), 7.55 (m, 2H), 7.77 (m, 2H), 8.34 (br s, 1H, NH), 8.38 (d, 1H, J=8.0 Hz), 8.52 (m, 2H), 12.60 (br s, 1H, NH), 13.80 (br s, 1H, HCl).

$^{13}$C NMR (200 MHz, DMSO-d$_6$) δ: 34.32, 43.89, 55.28, 55.49, 100.14, 111.88, 112.66, 112.70, 113.06, 118.74, 120.68, 120.98, 121.18, 121.97, 122.72, 124.84, 125.71, 130.61, 130.86, 135.24, 138.53, 141.38, 147.37, 148.58, 149.21.

Elemental weight percentage calculated for C$_{25}$H$_{23}$N$_3$O$_2$.1.0HCl.1.2H$_2$O: C, 65.92; H, 5.84; N, 9.22. Found: C, 65.89; H, 5.93; N, 9.29.

Example 8

Preparation of Compound 8a: N,N-Bis-[3-(11H-indolo[3,2-c]quinolin-6-yl)aminopropyl]amine and its hydrochloride A mixture of 4a (1.26 g, 5 mmol), dipropylenetriamine (1.31 g, 10 mmol), pyridine (0.8 mL) and ethoxyethanol (20 mL) was heated in a sealed steel bomb at 100-120° C. for 4 days (TLC monitoring). The mixture was then cooled and evaporated in vacuo. The residue was treated with 1N HCl (30 mL). The resulting mixture was stirred at room temperature overnight. The mixture was filtered and the filtrate was treated with solid NaHCO$_3$ to neutralize excess HCl. The resulting precipitate was collected by filtration and then purified by FC (MeOH/CH$_2$Cl$_2$=⅕) to produce 8a (0.45 g, 16%) after crystallization from EtOH as a white powder. Mp: 107-108° C.

UV$_{\lambda max}$ nm (log ϵ): 242 (4.68), 267 (4.84), 350 (4.26) in MeOH; IR$_{\nu max}$ (cm$^{-1}$): 1612, 1645, 3384 in KBr.

$^1$H NMR (DMSO-d$_6$) δ: 2.21 (m, 4H), 3.16 (m, 4H), 4.16 (m, 4H), 7.38 (m, 2H), 7.51 (m, 2H), 7.57 (m, 2H), 7.70-7.78 (m, 4H), 8.52 (m, 4H), 8.75 (m, 2H), 9.41 (br s, 2H), 12.71 (br s, 2H), 13.84 (br s, 2H, HCl).

$^{13}$C NMR (200 MHz, DMSO-d$_6$) δ: 25.37, 42.46, 44.18, 100.39, 112.60, 112.88, 118.94, 121.02, 121.24, 121.96, 122.72, 124.87, 125.63, 130.52, 135.48, 138.52, 141.44, 149.22.

Elemental weight percentage calculated for C$_{36}$H$_{33}$N$_7$.2.4HCl3.0 H$_2$O: C, 61.31; H, 5.92; N, 13.90. Found: C, 61.33; H, 5.72; N, 13.83.

Example 9

Preparation of Compound 8b: N,N-Bis-[3-(11H-indolo[3,2-c]quinolin-6-yl)aminopropyl]-N-methylamine and its hydrochloride Compound 8b and its hydrochloride were obtained from 4a and N,N-bis(3-aminopropyl)methylamine in a manner similar to that described in Example 8. The hydrochloride was purified by recrystallization with EtOH to produce 8b as a white powder. Yield: 21%; Mp: 76-77° C.

UV$_{\lambda max}$ nm (log ϵ): 259 (4.59), 337 (3.79) in MeOH; IR$_{\nu max}$ (cm$^{-1}$): 1614, 1650, 3398 in KBr.

$^1$H NMR (DMSO-d$_6$) δ: 2.31 (m, 4H), 2.89 (s, 3H), 3.35-3.49 (m, 4H), 4.11 (m, 4H), 7.39 (m, 2H, Ar—H), 7.51 (m, 2H, Ar—H), 7.61 (m, 2H, Ar—H), 7.71-7.78 (m, 4H, Ar—H),), 8.45-8.50 (m, 4H, Ar—H), 8.55 (br s, 2H, NH), 8.66 (m, 2H, Ar—H), 10.60 (br s, 1H, NH), 12.71 (br s, 1H, NH), 13.64 (br s, 1H, HCl).

$^{13}$C NMR (200 MHz, DMSO-d$_6$) δ: 23.42, 40.21, 42.06, 52.19, 100.24, 112.49, 112.82, 118.88, 120.86, 121.15, 121.81, 122.65, 124.72, 125.48, 130.32, 135.40, 138.44, 141.36, 149.13.

Elemental weight percentage calculated for C$_{37}$H$_{35}$N$_7$.1.2HCl.0.9H$_2$O: C, 70.30; H, 6.11; N, 15.51. Found: C, 70.34; H, 6.04; N, 15.42.

Example 10

In Vitro Anticancer Assay

Compounds 5, 6, 7a, 8a, and 8b were evaluated in vitro against 60 human tumor cell lines derived from nine cancer cell types: leukemia (CCRF-CEM, HL-60 (TB), K-562, MOLT-4, RPMI-8226, and SR); non-small cell lung cancer (A549/ATCC, EKVX, HOP-62, HOP-92, NCI-H226, NCI-H23, NCI-H322M, and NCI-H522); colon cancer (COLO 205, HCC-2998, HCT-116, HCT-15, HT29, KM12, and SW-620); CNS cancer (SF-268, SF-295, SF-539, SNB-19, SNB-75, and U251); melanoma (LOX IMVI, MALME-3M, M14, SK-MEL-2, SK-MEL-28, SK-MEL-5, UACC-62, and UACC-257); ovarian cancer (IGROV1, OVCAR-3, OVCAR-4, OVCAR-5, OVCAR-8, and SK-OV-3); renal cancer (786-0, A498, ACHN, CAKI-1, RXF 393, SN12C, TK-10, and UO-31); prostate cancer (PC-3 and DU-145); and breast cancer (MCF7, MCF7/ADR-RES, MDA-MB-231/ATCC, HS 578T, MDA-MB-435, MDA-N, and T-47D). For each compound, dose-response curves for each cell line were measured with five different drug concentrations, and the concentration causing 50% cell growth inhibition (GI$_{50}$) compared with the control was calculated. The mean GI$_{50}$ values of each tested compound for all the 60 tumor cell lines were also calculated. Unexpectedly, compound 8b has a GI$_{50}$ value ranging from less than 0.01 μM to about 0.11 μM for each cell line (a mean GI$_{50}$ value of less than 0.02 μM); compound 8a has a GI$_{50}$ value ranging from about 0.01 μM to about 0.85 μM for each cell line (a mean GI$_{50}$ value of about 0.15 μM); compounds 5 and 6 each have a GI$_{50}$ value ranging from about 0.01 μM to about 1.26 μM for each cell line (a mean GI$_{50}$ value of about 0.30 μM); and compound 7a has a GI$_{50}$ value ranging from about 1.02 μM to about 2.89 μM for each cell line (a mean GI$_{50}$ value of about 1.70 μM).

Example 11

Telomeric Repeat Amplification Protocol (TRAP) Assay

The inhibition of telomerase activity in a cell-free assay by compounds 5, 6, 7a, 7b, 7c, 8a, and 8b was assessed with a modified TRAP assay. Total cell extracts were prepared from exponentially growing H1299 human lung cancer cells. The H1299 culture cells were washed with phosphate buffered saline (PBS) and then resuspended in lysis buffer containing 10 mM Tris Cl (pH 7.5), 1 mM MgCl$_2$, 1 mM ethylene glycol tetraacetic acid (EGTA), 10% glycerol, 5 mM β-mercaptoethanol, 0.1 mM phenylmethylsulfonyl fluoride, 0.5% 3-((3-cholamidopropyl)dimethylammonio)-1-propanesulfonic acid (CHAPS) and extracted for 30 min at 4° C. The extract was centrifuged at 20,000 g. The supernatant was divided into aliquots and frozen. The protein concentration was determined by Bradford assay. The TRAP assay was performed following the protocol described by Kim et al. (Kim N R, Piatyszek M A, Prowse K R, et al., "Specific association of human telomerase activity with immortal cells and cancer," Science 1994; 266:2011-5). A 40 μL reaction buffer was obtained, containing TRAP buffer (20 mM Tris-HCl, pH 8.3), 68 mM KCl, 1.5 mM MgCl$_2$, 1 mM EGTA, 0.05% v/v Tween 20), 50 μM of each deoxynucleotide triphosphate, and 0.1 μg of TS primer (TS: 5'-AATCCGTCGAGCAGAGTT-3'). The cell extract (0.5 μg) was then incubated with the reaction buffer for 30 min at 25° C. in the presence or absence of a test compound. RNase A was mixed with the cell extract before the incubation in a control. Telomerase activity was then inactivated at 94° C. in a PCR block of a thermal cycler for 5 min. 0.1 μg of reverse CX primer (5'-CCCTTACCCTTAC-CCTTACCCTAA-3') and 2 units of Taq DNA polymerase were added. A three-step PCR was then performed: 94° C. for 30 s, 55° C. for 30 s, and 72° C. for 1 min for 33 cycles. The telomerase-extended PCR products were resolved by 10% polyacrylamide gel electrophoresis and visualized by staining with SYBER Green. Unexpectedly, compounds 5, 6, 8a, and 8b at a concentration of 0.02 μM, compound 7b at a concentration of 0.2 µM, and compounds 7a and 7c at a concentration of 2 µM inhibited telomerase activity effectively.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

2. The compound of claim 1, wherein X is NH, hydroxyimino, or alkoxyimino.

3. A compound of formula (I):

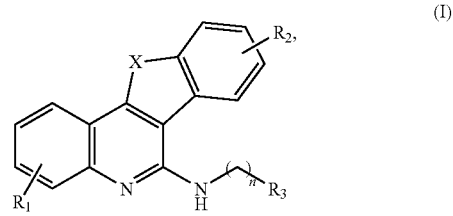

What is claimed is:

1. A compound of formula (I):

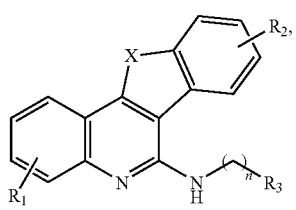

in which
  X is O, S, NH, hydroxyimino, or alkoxyimino;
  $R_1$ is H, halo, alkyl, OH, alkoxyl, nitro, amino, alkylamino, or dialkylamino;
  $R_2$ is H, halo, alkyl, nitro, amino, alkylamino, or dialkylamino;
  $R_3$ is phenyl, or piperazinyl; and
  n is 1, 2, 3, or 4.

in which
  X is O, S, NH, hydroxyimino, or alkoxyimino;
  $R_1$ is H, halo, alkyl, OH, alkoxyl, nitro, amino, alkylamino, or dialkylamino;
  $R_2$ is H, halo, alkyl, nitro, amino, alkylamino, or dialkylamino;
  $R_3$ is —N(A)-B in which A is H, alkyl, aryl, heteroaryl, cycloalkyl, or heterocycloalkyl and B is alkyl containing 1-6 N atoms; and
  n is 1, 2, 3, or 4.

4. The compound of claim 3, wherein B is of formula (II)

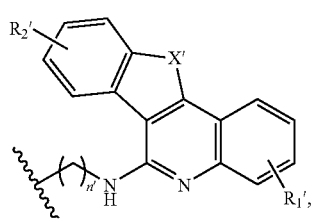

in which
X' is O, S, NH, hydroxyimino, or alkoxyimino;
each of $R_1'$ and $R_2'$, independently, is H, halo, alkyl, OH, alkoxyl, nitro, amino, alkylamino, or dialkylamino; and
n' is 1, 2, 3, or 4.

5. The compound of claim 4, wherein X' is NH, hydroxyimino, or alkoxyimino.

6. The compound of claim 5, wherein X is NH, hydroxyimino, or alkoxyimino.

7. A compound of formula (I):

(I)

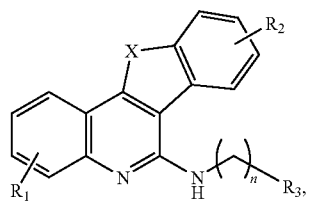

in which
X is O, S, NH, hydroxyimino, or alkoxyimino;
each of $R_1$ and $R_7$, independently, is H, halo, alkyl, OH, alkoxyl, nitro, amino, alkylamino, or dialkylamino;
$R_3$ is phenyl, alkylpiperazinyl, or —N(A)-B in which A is H, alkyl, aryl, heteroaryl, cycloalkyl, or heterocycloalkyl and B is alkyl containing 1-6 N atoms; and
n is 1, 2, 3, or 4.

8. The compound of claim 7, wherein B is alkyl containing 1-6 N atoms.

9. The compound of claim 8, wherein B is of formula (II)

(II)

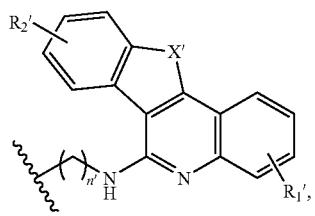

in which
X' is O, S, NH, hydroxyimino, or alkoxyimino;
each of $R_1'$ and $R_2'$, independently, is H, halo, alkyl, OH, alkoxyl, nitro, amino, alkylamino, or dialkylamino; and
n' is 1, 2, 3, or 4.

10. The compound of claim 9, wherein X' is NH, hydroxyimino, or alkoxyimino.

11. The compound of claim 7, wherein X is NH, hydroxyimino, or alkoxyimino.

12. The compound of claim 7, wherein the compound is one of

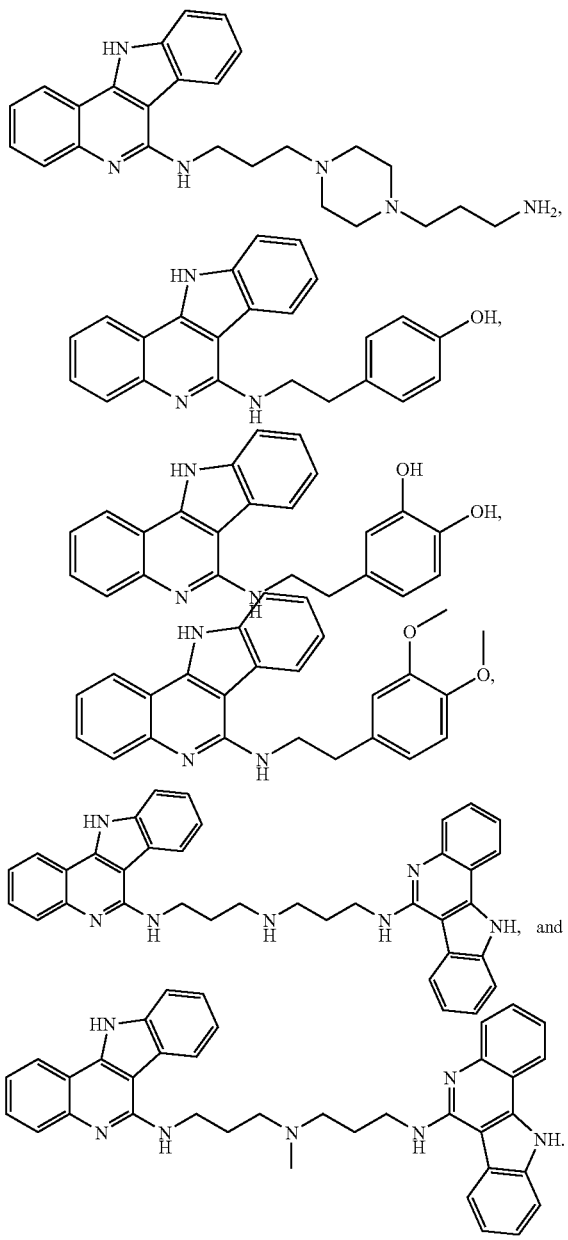

13. A pharmaceutical composition, comprising a compound of claim 7 and a pharmaceutically acceptable carrier.

14. A pharmaceutical composition, comprising a compound of claim 1 and a pharmaceutically acceptable carrier.

15. The compound of claim 1, wherein the compound is

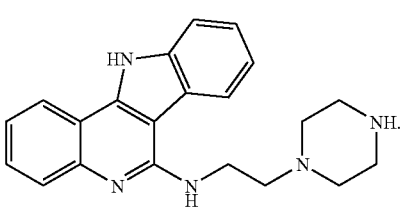

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: PCR Primer

<400> SEQUENCE: 1
aatccgtcga gcagagtt                                                18

<210> SEQ ID NO 2
<211> LENGTH: 24
<212> TYPE: DNA
<213> ORGANISM: Artificial Sequence
<220> FEATURE:
<223> OTHER INFORMATION: PCR Primer

<400> SEQUENCE: 2
cccttaccct tacccttacc ctaa                                         24
```